United States Patent
Silver (10) Patent No.: US 9,566,457 B2
(45) Date of Patent: Feb. 14, 2017

(54) USE OF HYDROPHILIC-RICH ALKYLMETHYLSILOXANE-DIMETHYL SILOXANE-POLYOXYALKYLENE COPOLYMERS AS EMULSIFIERS FOR THE PREPARATION OF COSMETIC O/W EMULSIONS OF IMPROVED AESTHETIC PROPERTIES AND MILDNESS

(76) Inventor: Michael E. Silver, Holland, MI (US)

( * ) Notice: Subject to any disclaimer, the term of this patent is extended or adjusted under 35 U.S.C. 154(b) by 0 days.

(21) Appl. No.: 12/658,594

(22) Filed: Aug. 15, 2011

(65) Prior Publication Data

US 2012/0149931 A1   Jun. 14, 2012

Related U.S. Application Data

(63) Continuation of application No. 11/599,171, filed on Nov. 13, 2006, now abandoned, which is a
(Continued)

(51) Int. Cl.
*A61K 9/00* (2006.01)
*A61Q 19/00* (2006.01)
(Continued)

(52) U.S. Cl.
CPC ............ *A61Q 19/00* (2013.01); *A61K 8/06* (2013.01); *A61K 8/062* (2013.01); *A61K 8/894* (2013.01);
(Continued)

(58) Field of Classification Search
CPC ...................................................... A61K 8/06
See application file for complete search history.

(56) References Cited

U.S. PATENT DOCUMENTS

6,433,244 B1 *   8/2002   Roe et al. ................. 604/361

* cited by examiner

Primary Examiner — Paul Dickinson
(74) Attorney, Agent, or Firm — King & Partners, PLC

(57) ABSTRACT

This invention relates to the use of hydrophilic-rich, rake-type alkylmethylsiloxane-dimethylsiloxane-polyoxyalkylene copolymers.

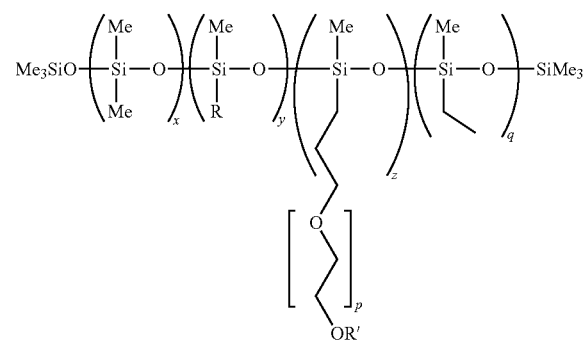

typical values (ranges)
x=10-30
y=2-6
z+q=4-5 (q≤0.8)
p=12
R=dodecyl
R'=H, Me

A hydrophilic-rich alkylmethylsiloxane-dimethylsiloxane-polyoxyalkylene copolymer is hereby defined as an alkylmethylsiloxane-dimethylsiloxane-polyoxyalkylene copolymer possessing sufficient hydrophilic content such that it can be readily taken up by water at a concentration of at least 15% by mass copolymer with simple stirring at room temperature to yield a stable dispersion of micron and sub-micron sized particles. This definition supercedes the typical values of the formula variables x, y, z, q, and p specified above to include all values that result in the
(Continued)

copolymer being hydrophilic-rich. This definition also supercedes the typical identity of R=dodecyl shown above to include R being any alkyl or branched-alkyl chain of any length such that the resulting copolymer is hydrophilic-rich. This definition also supercedes the typical identity of the polyoxyalkylene shown above to include polyoxyalkylenes possessing propylene oxide repeat units as well as ethylene oxide repeat units such that the resulting copolymer is hydrophilic-rich. This definition also supercedes the typical identity of R'=H, Me shown above to include any alkyl, aryl, or acyl radical such that the resulting copolymer is hydrophilic-rich. This invention also relates to the use of these copolymers as emulsifiers for the preparation of cosmetic O/W formulations (defined as stable O/W emulsions of water, one or more oils that may include silicone oils, and various other ingredients that may include preservatives, fragrances, coloring agents, etc.) that yield improved aesthetic properties (including appearance and texture of the cosmetic emulsion, initial feel on the skin, and final feel on the skin after rub-out) and improved mildness relative to comparable cosmetic emulsions that employ other silicone-copolymer emulsifiers as well as other non-silicone emulsifiers.

1 Claim, 2 Drawing Sheets

Related U.S. Application Data continuation of application No. 11/107,325, filed on Apr. 13, 2005, now abandoned, which is a continuation of application No. 10/891,438, filed on Jul. 14, 2004, now abandoned.

(60) Provisional application No. 60/487,179, filed on Jul. 14, 2003, provisional application No. 60/513,136, filed on Oct. 21, 2003.

(51) Int. Cl.
 *A61K 8/06* (2006.01)
 *A61K 8/894* (2006.01)
 *A61K 31/74* (2006.01)
 *A61Q 1/14* (2006.01)
 *A61Q 17/04* (2006.01)

(52) U.S. Cl.
 CPC ............ *A61K 31/74* (2013.01); *A61Q 1/14* (2013.01); *A61Q 17/04* (2013.01)

USE OF HYDROPHILIC-RICH ALKYLMETHYLSILOXANE-DIMETHYL SILOXANE-POLYOXYALKYLENE COPOLYMERS AS EMULSIFIERS FOR THE PREPARATION OF COSMETIC O/W EMULSIONS OF IMPROVED AESTHETIC PROPERTIES AND MILDNESS

CROSS-REFERENCE TO RELATED APPLICATIONS

This application is a continuation of U.S. application Ser. No. 11/599,171, filed Nov. 13, 2006, which is a continuation of U.S. application Ser. No. 11/107,325, filed Apr. 13, 2005, which is a continuation of U.S. application Ser. No. 10/891,438, filed Jul. 14, 2004, which claims the benefit of U.S. Provisional Application Ser. No. 60/487,179 filed Jul. 14, 2003, and U.S. Provisional Application Ser. No. 60/513,136 filed Oct. 21, 2003, all of which are hereby incorporated herein by reference in their entirety.

BACKGROUND OF THE INVENTION

1. Field of the Invention

The invention present invention relates to novel, hydrophilic-rich organomethylsiloxane-dimethylsiloxane-polyoxyalkylene copolymers and to their use as emulsifiers for the preparation of cosmetic emulsions of improved aesthetic properties and mildness.

2. Background Art

An emulsion is a dispersion of droplets of one liquid in a second, immiscible liquid.

The process of dispersing one liquid in a second immiscible liquid is called emulsification.

An emulsifier is required to stabilize an emulsion. Emulsifiers are surface-active agents, that is a soluble compound that reduces the surface tension of liquids, or reduces the interfacial tension between two liquids. Surface tension is the force acting on the surface of a liquid, tending to minimize the area of the surface. Surfactants and emulsifiers (all emulsifiers are a class of surfactants) reduce the surface tension of a liquid. The surface tension of water is 72 dyne/cm; a surfactant can reduce this to a value in the range of 30-50 dyne/cm.

There are two basic types of emulsions: oil in water (o/w) and water in oil (w/o). The substance named last indicates the continuous or outer phase. Whether a particular oil and water blend will form a w/o or o/w emulsion depends largely on the choice of emulsifier. Emulsifiers that are more soluble in water than in the oil generally produce o/w emulsions. Emulsifiers that are more soluble in the oil produce w/o emulsions.

Choice of emulsifier type is dependant upon the final skin feel desired. The continuous phase will be the most perceived phase while applying the lotion and after dry down. Water in oil emulsions (w/o) tend to be heavier, leave a more distinctive after-feel and are considered warmer than emulsions with water as the continuous phase (o/w). When water is the continuous or outer phase, typically the formulation is lighter, easier to rub in to the skin, and the after-feel is lighter. The overall skin conditioning efficacy of both emulsion types o/w and w/o is dependant on the relative concentrations of the ingredients used.

A predominantly hydrophilic emulsifier, will best stabilize o/w emulsions, while a predominantly lipophilic emulsifier, will best stabilize w/o emulsions.

HLB, the hydrophile/lipophile balance of a surfactant, can help determine the best surfactants to use as emulsifiers. As expected, products with higher ethylene oxide content are more suitable for o/w emulsification, while products with lower ethylene oxide content are more suitable for w/o emulsification.

A review of predominant skin care products currently in the market shows strong regional preferences for specific emulsion types. Typically European markets sell heavier, more occlusive formulations and as such have a strong preference for w/o formulations. Outside of the European markets, the overwhelming global preference of lotions is o/w. This preference is most predominant in Asian markets. The o/w formulations provide excellent skin treatment products without leaving excessively coated heavy feeling. This is most preferable in hot humid environments. Very few if any w/o formulations are even sold in Asia. The United States and Latin American markets also have strong preferences toward the lighter feeling o/w formulation, however there are some brands sold using w/o technology.

The alkyl dimethicone copolyol emulsifiers of this invention are unique in that they serve as o/w emulsifiers and provide stable o/w emulsions. This is in contrast to alkyl dimethicone copolyol emulsifiers of the prior art (see, for example, U.S. Pat. No. 4,698,178), which specifically serve as w/o emulsifiers and provide stable w/o emulsions. The alkyl dimethicone copolyol emulsifiers of this invention have an additional benefit of providing lift from the surface, creating an overall skin feel that is soft and extremely smooth. This softening effect is important beyond aesthetics in that it reduces the overall roughness of the surface of the skin, allowing light to reflect more evenly. The skin appears more uniform in color and texture, a benefit strongly desired in anti-aging skin care products. This benefit is not observed using either the aforementioned alkyl dimethicone copolyol w/o emulsifiers of the prior art (such as Goldschmidt ABIL EM90) or o/w emulsifiers of the dimethicone copolyol variety (such as Dow Corning DC 193) or o/w emulsifiers of the non-silicone containing variety (such as Glyceryl Stearate and PEG 100 Stearate). Additional benefits provided by the emulsifiers of this invention over the aforementioned emulsifiers are a reduction of greasy feeling for emulsions that have high (15% or higher) oil and/or petrolatum content, a brilliant white appearance and less dense, soufflé-like texture for said high oil and or petrolatum emulsions, a decreased rub in time, a final rub out that is less greasy, and a markedly decreased irritancy.

There is considerable prior art relating to polydimethylsiloxane-polyoxyalkylene copolymers (silicone copolyols) and organomethylsiloxane-dimethylsiloxane-polyoxyalkylene copolymers (organo-functional silicone copolyols).

Organo-functional silicone copolyols related to those of this invention have been prepared from silicon hydride containing siloxanes of the general structure $$Me_3SiO(Me_2SiO)_x(HMeSiO)_ySiMe_3$$

wherein Me is methyl, x is 0 to about 200, and y is about 1 to 100, via a hydrosilation coupling reaction (that utilizes a platinum catalyst) with terminally unsaturated polyoxyalkylenes and terminally unsaturated organic molecules. The synthesis of organo-functional silicone copolyols is described in U.S. Pat. Nos. 3,234,252, 4,047,958, 3,427,271, 2,846,458, and 6,346,553, and yields products of the general formulas $$Me_3SiO(Me_2SiO)_x(MeRSiO)_y(MeQSiO)_zM$$

$$QMe_2SiO(Me_2SiO)_x(MeRSiO)_ySiOMeQ$$

wherein R denotes an alkyl radical and Q denotes a polyoxyalkylene radical having the formula —CH$_2$CH$_2$CH$_2$ $(OCH_2CH_2)_p(OCH_2CHCH_3)_qOR'$ wherein R'=H or Me and both p and q range between 0-50. These preparations are similar to those for the preparation of silicone copolyols. The preparation of such copolymers by the platinum catalyzed hydrosilation of silicon hydride containing siloxanes and a polyoxyalkylene that is allyl terminated at one end and either OMe or O(CO)R terminated at the other end is well known and straightforward. The similar preparation of silicone copolyols that employ polyoxyalkylene but that is allyl terminated at one end and OH terminated at the other end is more problematic. In all reported cases prior to this invention, steps are taken in an attempt to eliminate or minimize competing crosslinking side reactions that involve the polyoxyalkylene terminal OH function and are well know to those practiced in the art. One such crosslinking side reaction is due to reaction of the Si—H and COH groups. Another is conversion of terminal allyl groups to propenyl groups followed by crosslinking via acetal formation with a polyoxyalkylene OH terminus. These crosslinking reactions are catalyzed by platinum catalysts such as chloroplatininc acid ($H_2PtCl_6 \cdot 6H_2O$), and lead to a generally undesired increase in viscosity of the final product and/or eventual gellation.

Much of the prior art relating to the preparation of silicone copolyols, embodied in U.S. Pat. Nos. 3,280,160, 3,401,192, 4,122,029, 3,518,288, 4,520,160, 5,958,448, 6,346,583, and 6,346,595, discloses the use of one or more solvents, often a small cyclic polydimethylsiloxane or an alcohol, to minimize the aforementioned side reactions. A solventless process is disclosed in U.S. Pat. Nos. 4,847,398 and 6,372,874 that employ catalyst modifiers which also minimize the aforementioned crosslinking side reactions. In U.S. Pat. No. 4,025,456, a solventless process for the preparation of siloxane-polyoxyalkylene copolymers is revealed. This reference, however, utilizes alkoxy endblocked polyethers in the hydrosilation reaction and does not disclose the use of OH terminal oxyalkylene polyethers.

Similarly, much of the prior art relating to the preparation of organo-functional silicone copolyols discloses the use of one or more solvents or endblocked (protected) polyethers to minimize the aforementioned side reactions. In U.S. Pat. No. 6,346,553, a solventless process for the preparation of organo-functional silicone copolyols is revealed that utilizes alkoxy endbolcked polyethers. Another common method is to protect the polyoxyalkylene OH termini via conversion to $OSiMe_3$, followed by deprotection after hydrosilation, as is the case in U.S. Pat. No. 2,846,458.

Silicone copolyols and organo-functional silicone copolyols are commonly used as emulsifiers for the preparation of cosmetic formulations, a fact well known to those practiced in the art. Typical examples of silicone copolyols are $Me_3SiO(Me_2SiO)_{22}(MeQSiO)_4SiMe_3$ and $Me_3SiO(Me_2SiO)_{8.7}(MeQSiO)_{3.7}SiMe_3$ (where $Q=(CH_2)_3(OCH_2CH_2)_{12}OH$). These and similar materials are "water soluble" (i.e., they are either truly soluble or they form stable dispersions in water). According to U.S. Pat. Nos. 4,381,241, and 4,698,178, rake-type organo-functional silicone copolyols of the type $Me_3SiO(Me_2SiO)_x(MeRSiO)_y(MeQSiO)_zM$ can also be used as emulsifiers for the preparation of cosmetic emulsions. The ABA or end-blocked organo-functional silicone copolymers $QMe_2SiO(Me_2SiO)_x(MeRSiO)_ySiOMeQ$ of U.S. Pat. No. 6,346,553 can be used as emulsifiers for the preparation of combined oil-silicone O/W emulsions. In all of these cases, the preferred formula is one in which the number of units having alkyl (R) radicals is at least twice as large (and typically much greater than twice as large) as the number of units with polyoxyalkylene (Q) radicals. This preference, along with the preferred length of the alkyl radical and the preferred composition of the polyoxyalkylene radical (which generally includes water insoluble propylene oxide units along with water soluble ethylene oxide units) results in predominantly hydrophobic (water insoluble) organo-functional silicone copolyols. One such example, a rake-type alkylmethylsiloxane-dimethylsiloxane-polyoxyalkylene emulsifier of the type described in U.S. Pat. No. 4,698,178, is available under the name Goldschmidt ABIL EM90 and is insoluble in water. Thus, whereas organo-functional silicone copolyols of the prior art are insoluble in water, the organo-functional silicone-copolyol emulsifiers of this invention are soluble in that they form stable dispersions in water at ≥15% mass emulsifier.

Many modern cosmetic formulations that make use of emulsifiers of the type described above and/or other emulsifiers have a high oil content (>20% by mass oils). Desirable aesthetic effects for such cosmetic formulations include a light texture, an initial rub-in that possesses a light, slightly wet, cool feel (as opposed to a heavy, greasy, warm feel), a short overall rub-in time, and a final rub-out that is not heavy, greasy, or tacky, but instead leaves a light occlusive barrier on the skin. Also desirable is a minimization of skin irritancy (i.e., maximum mildness). Emulsifiers that can bestow these properties to cosmetic formulations would be desirable and valuable.

SUMMARY OF THE INVENTION

We have prepared a class of hydrophilic-rich organo-functional silicone copolyols that are intermediate in behavior between the well-known silicone copolyols and organo-functional silicone copolyols. By hydrophilic-rich, it is meant that the copolymer can be easily taken up by water at a concentration of about ≥15% by mass copolymer with simple stirring to yield a stable dispersion of micron and sub-micron sized particles. Such behavior is typical for silicone copolyols (which are typically hydrophilic to the point that they form the aforementioned dispersions or they are completely water soluble), but not for organo-functional silicone copolyols of the prior art (which are preferably water insoluble and predominantly hydrophobic). The organo-functional silicone copolyols of this invention are thus intermediate in that they are organo-functional but are intentionally designed to contain sufficient hydrophilic character such that they form the aforementioned dispersions in water at a concentration of about ≥15% by mass copolymer with simple stirring. In addition, the hydrophilic-rich organo functional silicone copolymers of this invention function as emulsifiers for high oil content (>20% by mass) cosmetic o/w formulations such that, when compared to similar cosmetic formulations employing either (a) traditional non-silicone emulsifiers such as glycerol stearate+PEG 100 stearate emulsifiers, or (b) organo-functional silicone copolymer emulsifiers such as Goldschmidt ABIL EM90, or (c), silicone copolymer emulsifiers such as $Me_3SiO(Me_2SiO)_{8.7}(MeQSiO)_{3.7}SiMe_3$ (where $Q=(CH_2)_3(OCH_2CH_2)_{12}OH$), result in a much improved set of aesthetic set of properties including (1) a lighter texture, (2) an initial rub-in that has a lighter, wetter, and cooler feel, (3) a shorter overall rub-in time, and (4) a final rub-in that is less-tacky, less greasy, and leaves a lighter feeling occlusive barrier on the skin] and increased mildness as measured by cyto-toxicity tests.

BRIEF DESCRIPTION OF THE DRAWINGS

The invention will now be described with reference to the drawings wherein.

DETAILED DESCRIPTION OF THE INVENTION

While this invention is susceptible of embodiment in many different forms, there is described herein in detail several specific embodiments with the understanding that the present disclosure is to be considered as an exemplification of the principles of the invention and is not intended to limit the invention to the embodiments illustrated.

The present invention was accomplished by using, as an emulsifier for the preparation of cosmetic emulsions (both W/O and O/W) with high oil content, organo-functional silicone copolyols of this invention, which have the following nominal formula:

Typical Ranges
R is an alkyl radical with 12 to 16 carbon atoms
R' is an alkyl, aryl, acyl, or hydrogen radical
$x = 10\text{-}20$
$y = 2\text{-}6$
$z = 3\text{-}5$
$q < 0.8$
$p = 7\text{-}20$
with the proviso that x is $\leq 3(y+z+q)$ and
$y \leq 2z$, resulting in hydrophilic-rich material.

Organo-functional silicone copolyols of the previous art (see for example, U.S. Pat. No. 4,698,718) have a preferred formula in which the number of units having alkyl radicals is at least twice as large ($y > 2z$) and typically much greater than twice as large as the number of units with polyoxyalkylene radicals, rendering them predominantly hydrophobic. The organo-functional silicone copolyols of this invention have preferred formula such that $y \leq 2z$ (the number of units having alkyl radicals is less than or equal to 2 times the number of units with polyoxyalkylene radicals), which functions to render the copolymers hydrophilic-rich (i.e., they are readily taken up by water and simple stirring to form stable dispersions at 15% by mass copolymer). Secondly, the number of dimethylsiloxane units is adjusted to be no more than three times the sum of the number of alkylmethysiloxane and polyoxyalkylene units [$x < 3(y+z+q)$], which also functions to render the copolymers of this invention hydrophilic rich. Thirdly, the copolymers of this invention typically employ polyoxyethylene copolymers, whereas the copolymers disclosed in U.S. Pat. No. 4,698,178 employ polyoxyalkylenes that are oxyethylene-oxypropylene copolymers of the type $(C_2H_4O-)_x(C_3H_6O-)_yR$ with preferred weight ratio of oxyethylene to oxypropylene groups from 40:60 to 70:30. Oxypropylene groups render the polyoxyalkylene less hydrophilic. The preferred use for this invention of polyoxyalkylenes with no oxypropylene component (only oxyethylene component) further increases the hydrophilic content of the copolymers of this invention.

The hydrophilic-rich organo-functional silicone copolyols of this invention may be used as primary emulsifiers or may also be used in combination with known emulsifiers such as glyceryl stearate, PEG 100 stearate, oleth-3, etc. Those skilled in the art know that emulsifier mixtures frequently enable stable emulsions to be prepared.

The oil phase may contain silicone oils. Within the meaning of the present invention, silicone oils are liquid to very viscous gels, particularly linear or cyclic, organosilicon compounds, whose silicon units are predominantly difunctional and correspond to the formula $$\left[ \begin{array}{c} R^1 \\ | \\ Si-O- \\ | \\ R^2 \end{array} \right]_p$$

The $R^1$ and $R^2$ radicals may be the same or different and are hydrocarbon radicals, especially alkyl or aryl radicals, with methyl or phenyl radicals being especially preferred. A portion of the $R^1$ and $R^2$ radicals may be hydrogen radicals; p is a number not less than 2. The silicone oils may have an end group and especially may be groups having the formula $(R^1, R^2)_3SiO-$ or hydroxyl groups. Trifunctional silicon units of formula $(R^1, R^2)SiO_{1.5}-$ may also be contained in small amounts. The viscosity of the silicones usually falls within the range of 0.5 mPa sec to $3 \times 10^5$ mPa sec.

The oily phase of the emulsions may contain carbon based oils, waxes, or petrolatum in addition to the silicone oil. An example of these oils include isopropyl palmitate.

The preparation of the desired emulsion is accomplished in a know manner. The emulsifier of this invention is used either as 15% by mass aqueous dispersion or as the pure material. Advisably, the aqueous dispersion is added to the aqueous phase, whereas the pure material is added to the oil phase. The procedure is then as follows: (1) Heat the aqueous phase and the oil phase separately to 70° C. (2) When both phases are at 70° C., add the oil phase to the water phase with stirring. (3) Cool to 45° C. (4) Add the neutralizer and preservative phase. (5) Cool to room temperature with mixing.

The following examples (as set forth in the Table below) illustrate the composition of high-oil phase emulsions prepared using emulsifiers of this invention as well as representative commercially available emulsifiers.

|  | Control | A* | B | C** |
|---|---|---|---|---|
| WATER PHASE | | | | |
| Water | 67.65 | 69.65 | 67.65 | 67.65 |
| Carbomer 980 | 0.10 | 0.10 | 0.10 | 0.10 |
| Glycerin | 2.00 | 2.00 | 2.00 | 2.00 |
| Glycereth-26 | 3.00 | 3.00 | 3.00 | 3.00 |

-continued

|  | Control | A* | B | C** |
|---|---|---|---|---|
| Methylparaben | 0.25 | 0.25 | 0.25 | 0.25 |
| Emulsifier of this invention | 0.00 | 3.00 | 0.00 | 0.00 |
| Glyceryl Stearate & PEG 100 Stearate emulsifiers | 5.00 | 0.00 | 0.00 | 0.00 |
| OIL PHASE | | | | |
| Isopropyl Palmitate | 7.00 | 7.00 | 7.00 | 7.00 |
| Petrolatum | 7.50 | 7.50 | 7.50 | 7.50 |
| Behenyl Alcohol | 2.50 | 2.50 | 2.50 | 2.50 |
| Sorbitan Stearate | 1.00 | 1.00 | 1.00 | 1.00 |
| Dimethicone | 0.50 | 0.50 | 0.50 | 0.50 |
| Goldschmidt ABIL EM-90 emulsifier | 0.00 | 0.00 | 5.00 | 0.00 |
| Emulsifier of this invention | 0.00 | 0.00 | 0.00 | 5.00 |
| NEUTRALIZER AND PRESERVATIVE PHASE | | | | |
| Water | 2.00 | 2.00 | 2.00 | 2.00 |
| Triethanolamine | 0.50 | 0.50 | 0.50 | 0.50 |
| Benzyl Alcohol | 1.00 | 1.00 | 1.00 | 1.00 |
| TYPE OF EMULSION FORMED | | | | |
|  | O/W | O/W | W/O | O/W |

*Emulsifier of this invention is a 15% aqueous emulsion of the copolymer with R = dodecyl, R' = H, x = 18, y = 6, z + q = 4, q ≤ 0.8, p = 12.
**Emulsifier of this invention is the pure copolymer with R = dodecyl, R' = Me, x = 18, y = 5, z + q = 4, q ≤ 0.8, p = 12.

The control emulsion and emulsion B that employed the commercially available stearate and organo-functional silicone copolyols emulsifiers, respectively, were similar in that they produced a warm, greasy initial feel, possessed a long rub-in time, and gave rise to a final rub-out that was heavy and oily and left a heavy occlusive barrier on the skin. In addition, emulsion B employing Goldschmidt ABIL EM90 had a slippery, silicone feel and was off white in color. Emulsions A and C employing emulsifiers of this invention were a brilliant white color, possessed a light, soufflé-like texture, applied with a light, cool, wet feel, possessed a shorter rub-in time, and gave rise to a final rub-out that was light, less oily, and left a light occlusive barrier on the skin.

Emulsifiers of this invention also result in cosmetic formulations that are milder (less irritating to the skin) relative to similar formulations employing other emulsifiers as measured via cell culture cell-survival tests (so called cytotoxicity tests) for eye-makeup remover formulations based on MTT data from cells treated with test reagent for the indicated time (as set forth in the following Table).

| Sample | % Control viability 2 hrs | % Control viability 6 hrs | % Control viability 24 hr | $t_{50}$ (hrs) |
|---|---|---|---|---|
| A | 99.0 | 93.4 | 48.8 | 24 |
| Negative Ctrl | 100 | 100 | 100 | na |
| Positive Ctrl | 17.9 | 5.4 | 5.9 | <1 |
| B | 90.5 | 67.4 | 4.5 | ~11 |
| C | 87.6 | 65.5 | 19.7 | ~12.5 |

Results are the averages of treatments divided by the average of the negative control. $t_{50}$ were estimated from the graphic results. MTT (3-[4,5-dimethylthiazol-2-yl]-2,5-diphenyltetrazolium bromide) is a water-soluble chemical. Active mitochondrial dehydrogenases of living cells convert the yellowish MTT to an insoluble purple formazan. This conversion does not take place in dead cells. This water-insoluble formazan can be solubilized using isopropanol, and the dissolved material can be measured spectrophotometrically. The $t_{50}$ value is the time of exposure to test reagent (samples A-C) that reduced MTT metabolism to 50% of control levels.

The formulations A-C consisted of cyclomethicone (48%), dimethicone (2%), butylene glycol (8%) and preservatives (1%). Sample A employed 5% of Example 4 as the emulsifier and the remainder was water. Sample B employed 5% Dow Corning DC 193 as the emulsifier (a silicone polyethyleneglycol-copolyol) and the remainder was water. Sample C employed oleth-3 as the emulsifier and was anhydrous, employing petrolatum instead of water. The results clearly indicate significantly enhanced cell survivability for sample A, supporting the claim of increased mildness.

The following examples (as set forth in the Table below) illustrate the composition of various stable w/o emulsions prepared using emulsifiers of this invention.

| Formula Description | INCI Name | % |
|---|---|---|
| High Oil Phase Make-Up Remover | Cyclomethicone | 48.00 |
| Oil in Water Emulsion | Dimethicone | 2.00 |
|  | Example 6 Emulsifier (15% aqueus dispersion) | 5.00 |
|  | Deionized Water | 39.25 |
|  | Butylene Glycol | 3.00 |
|  | Glycein | 2.00 |
|  | Phenoxyethanol, Methylparaben, Ethylparaben, Propylparaben, Butylparaben | 0.75 |
|  |  | 100.00 |
| Sprayable Lotion | Deionized Water | 90.85 |
| Oil in Water Emulsion | Example 8 Emulsifier (5% aqueous dispersion) | 5.00 |
|  | Botanical Extracts | 2.00 |
|  | Propylene Glycol, Diazolidinyl Urea, Methylparaben, Propylparaben | 0.75 |
|  | C12-15 Alkyl Benzoate | 0.50 |
|  | Polysorbate 20 | 0.75 |
|  | Fragrance | 0.15 |
|  | FD&C Red No. 4 | trace |
|  |  | 100.00 |
| TiO2 Sunscreen Lotion | Deionized Water | 63.55 |
| Oil in Water Emulsion | Carbomer | 0.20 |
|  | Glyceryl Polymethacrylate | 10.00 |
|  | Glycerin | 1.50 |
|  | Butylene Glycol | 4.50 |
|  | Methylparaben | 0.25 |
|  | Disodium EDTA | 0.05 |
|  | Polysorbate 20 | 0.50 |

| Formula Description | INCI Name | % |
|---|---|---|
| | Squalane | 3.00 |
| | Dimethicone | 2.00 |
| | Petrolatum | 3.00 |
| | Example 8 Emulsifier (5% aqueous dispersion) | 4.00 |
| | Polyethylene | 0.50 |
| | 40% TiO2 in C12-15 Alkyl Benzoate | 6.00 |
| | Triethanolamine | 0.30 |
| | Phenoxyethanol, Methylparaben, Ethylparaben, Propylparaben, Butylparaben | 0.50 |
| | Fragrance | 0.15 |
| | | 100.00 |
| High Petrolatum Cream Oil in Water Emulsion | Water | 52.750 |
| | Carbomer 980 | 0.100 |
| | Glycerin | 2.000 |
| | Glycereth-26 | 3.000 |
| | Methylparaben | 0.250 |
| | Example 6 Emulsifer (15% aqueous dispersion) | 20.000 |
| | Isopropyl Palmitate | 7.000 |
| | Petrolatum | 7.500 |
| | Behenyl Alcohol | 2.500 |
| | Sorbitan Stearate | 1.000 |
| | Dimethicone | 0.500 |
| | Water | 2.000 |
| | Triethanolamine | 0.150 |
| | Benzyl Alcohol | 1.000 |
| | Fragrance | 0.250 |
| | | 100.000 |
| Emollient Lotion Oil in Water Emulsion | Water | 67.65 |
| | Carbomer 980 | 0.10 |
| | Glycerin | 2.00 |
| | Glycereth-26 | 3.00 |
| | Methylparaben | 0.25 |
| | Example 6 Emulsifier (15% aqueous dispersion) | 5.00 |
| | Isopropyl Palmitate | 7.00 |
| | Petrolatum | 7.50 |
| | Behenyl Alcohol | 2.50 |
| | Sorbitan Stearate | 1.00 |
| | Dimethicone | 0.50 |
| | Water | 2.00 |
| | Triethanolamine | 0.50 |
| | Benzyl Alcohol | 1.00 |
| | | 100.00 |

Experimental Procedure

Raw Materials

1. Preparation of Silanic Hydrogen Containing Intermediates

Silicone intermediates of the type used to make the compounds of this invention are well known to those skilled in the art. They conform to the following structure (the hydrogen containing units are randomly distributed):

These compounds were prepared from equilibration of octamethylcyclotetrasiloxane, hexamethyldisiloxane, and either tetramethylcyclotetrasiloxane or Me$_3$SiO—(MeHSiO)$_{50}$—SiMe$_3$, with tonsil acid clay (1 g per 100 g of reaction mixture) at 80° C. for a minimum of eight hours, filtered, and stripped of volatiles to 175° C. at 0.01 mm Hg.

The structures were confirmed using proton NMR spectroscopy. GPC analysis resulted in average molecular weights close to the calculated molecular weights listed below.

| Example | a | b | Calculated Molecular Weight (g/mole) |
|---|---|---|---|
| 1 | 18 | 9 | 2038 |
| 2 | 18 | 10 | 2098 |
| 3 | 27 | 9 | 2706 |

2. OH/Allyl and OMe/Allyl Terminal Polyoxyalkylenes

The Allyl/OH terminal polyoxyalkylene (polyether) used in this invention conforms to the following structure and is abbreviated in the examples below as Allyl/OH-PEO-12:

This compound was obtained from the Dow Corporation of Midland Mich. (DOW AE501) and from Goldschmidt AG of Essen Germany. These materials typically are wet, containing from 0.05% to 0.3% by mass water, and were used as is or were dried via azeotropic distillation of the water using toluene. The toluene was then removed via distillation. Drying made no significant change in the reaction or in the properties of the materials afterwards. One of the Allyl/OMe terminal polyoxyalkylenes used in this invention conforms to the following structure and is also abbreviated in the examples below as Allyl/OMe-PEO-12:

This compound was obtained from Goldschmidt AG of Essen Germany. This material typically is wet, containing approximately 0.12% by mass water, and was used as is or was dried via azeotropic distillation of the water using toluene. The toluene was then removed via distillation. Drying made no significant change in the reaction or in the properties of the materials afterwards. Another of the Allyl/OMe terminal polyoxyalkylenes used in this invention conforms to the following structure and is also abbreviated in the examples below as Allyl/0Me-PEO-10:

This compound was obtained from the Clariant Corporation and was used as is.

3. Alpha Olefins

The Alpha olefins used were 1-dodecene and ethylene, both available from a variety of sources.

Hydrosilation

All hydrosilation reactions were performed without solvent in a one liter heated Parr Model 4511 pressurizeable steel reactor equipped with two horizontally stacked pitched blade impellers and sampling port. The hydrosilation reaction used to make the compounds of this invention is well known to those skilled in the art. One of the many references is International Publication (Silicone Alkylene Oxide Copolymers As Foam Control Agents) WO 86/05411 by Paul Austin (Sep. 25, 1986) p. 19. A freshly prepared 0.050 M solution of $H_2PtCl_6 \cdot 6H_2O$ in 2-propanol was the source of platinum catalyst used to achieve a platinum concentration of 5 ppm for all reactions.

Preparation of Aqueous Dispersions and Determination of Dispersion Particle Size All of the copolymers of this invention form smooth, white 15% by mass dispersions in water. The dispersions were prepared as follows: (1) 200 g of neat copolymer were weighed into a 3-L round bottom flask followed by addition of sufficient room temperature RO (reverse osmosis) water (1133 mL) such that the resulting dispersion would be 15% by mass copolymer. (2) The water/copolymer combination was mechanically stirred at room temperature (mechanical stirrer employed a motor, and a glass shaft connected to a 76 mm length×19 mm width Teflon stir blade—Ace Glass Catalog item #8085-11) at approximately 480-500 rpm. After about 1 hour the dispersion appeared white and smooth, however, stirring was allowed to continue for a total duration of at least 8 hours.

Aqueous dispersion particle size was measured with the use of a Honeywell Microtrac UPA Particle Size Analyzer, which determines particle velocity distribution and size via measurement of Doppler shifts to the incident laser frequency at a single angle (dynamic light scattering technique). For this technique, aqueous dispersions of 1% concentration were employed (via appropriate dilution of the above 15% aqueous dispersion) and were filtered through a 0.45 μm filter to remove dust particles prior to study.

Molecular Weight Determination

Molecular weight determinations were made using a Water's System GPC with refractive index detection using a Phenomenex Phenogel 5 50 mm×7.80 mm guard column followed by a Phenomenex Phenogel 5 MXM 300 mm×7.8 mm 5 μm particle size 5 K-500 K column followed by a Phenomenex Phenogel 5 MXL 300 mm×7.8 mm 5 μm particle size 0K-40 K column in THF relative to polystyrene standards.

EXAMPLE 4

Copolymer where R=Dodecyl, R'=H, x=18, y=5, z+q=4, q≤0.8, p=12

Previously nitrogen saturated 1-dodecene (82.58 g, 0.491 mol), silanic hydrogen intermediate Example 1 (200.0 g, 0.0981 mol), and allyl/OH-PEO-12 (92.11 g, 0.157 mol) were combined in a Parr Model 4511 reactor and the head space was purged with nitrogen. The mixture was then stirred and heated to 85° C., whereupon the reactor was opened to allow for the injection of Pt catalyst (192.2 μL of a freshly prepared 0.050 M solution of $H_2PtCl_6 \cdot 6H_2O$ in isopropyl alcohol). The reactor was sealed and the head space again purged with nitrogen while stirring was initiated, resulting in an exotherm leading to a rapid approximate 35° C. increase in temperature. After 43 minutes, the reactor was opened and nitrogen saturated allyl/OH-PEO-12 (138.17 g, 0.235 mol) and additional Pt catalyst (70.7 μL) were added. The reactor was resealed and the stirred reaction allowed continued for an additional 67 minutes. By this time the reaction temperature was at 124° C. Next, the reactor was pressurized with 40 psi of ethylene and allowed to stir for an additional 50 minutes, during which time residual unreacted Si—H was consumed (monitored via IR spectroscopy). The maximum temperature reached during this interval was 125° C. The product, a clear, colorless semi-viscous liquid, was removed from the reactor and degassed of saturated ethylene in vacuo. Proton NMR spectra of the product were consistent with the expected structure.

EXAMPLE 5

Copolymer where R=dodecyl, R'=H, x=18, y=6, z+q=4, q≤0.8, p=12

Previously nitrogen saturated 1-dodecene (111.08 g, 0.660 mol), silanic hydrogen intermediate Example 2 (230.82 g, 0.110 mol), and allyl/OH-PEO-12 (103.22 g, 0.176 mol) were combined in a Parr Model 4511 reactor and the head space was purged with nitrogen. The mixture was then stirred and heated to 85° C., whereupon the reactor was opened to allow for the injection of Pt catalyst (215.3 μL of a freshly prepared 0.050 M solution of $H_2PtCl_6 \cdot 6H_2O$ in isopropyl alcohol). The reactor was sealed and the head space again purged with nitrogen while stirring was initiated, resulting in an exotherm leading to a rapid approximate 50° C. increase in temperature. After 30 minutes, the reactor was opened and nitrogen saturated allyl/OH-PEO-12 (154.88 g, 0.264 mol) and additional Pt catalyst (92.3 μl) were added. The reactor was resealed and the stirred reaction allowed continued for an additional 30 minutes. By this time the reaction temperature was at 106° C. Next, the reactor was pressurized with 40 psi of ethylene and allowed to stir for an additional 60 minutes, during which time residual unreacted Si—H was consumed (monitored via IR spectroscopy). The maximum temperature reached during this interval was 123° C. The product, a clear, colorless semi-viscous liquid, was removed from the reactor and degassed of saturated ethylene in vacuo. Proton NMR spectra of the product were consistent with the expected structure.

EXAMPLE 6

Copolymer where R=dodecyl, R'=Me, x=18, y=5, z+q=4, q≤0.8, p=12

Figure 1:
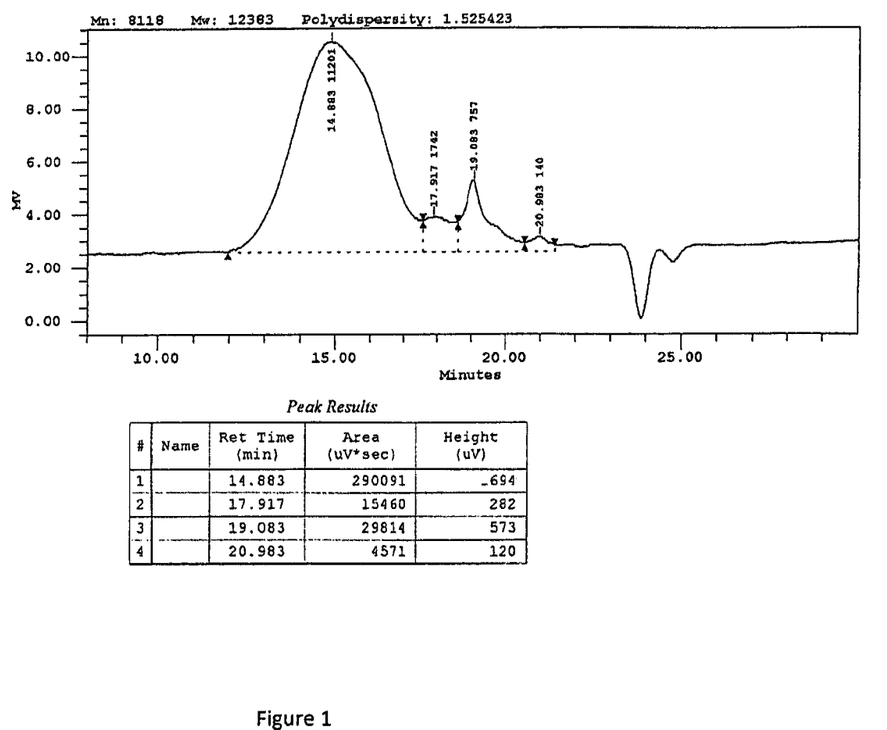
FIG. 1 of the drawings is a two-dimensional light scattering chromatogram.
Figure 2:
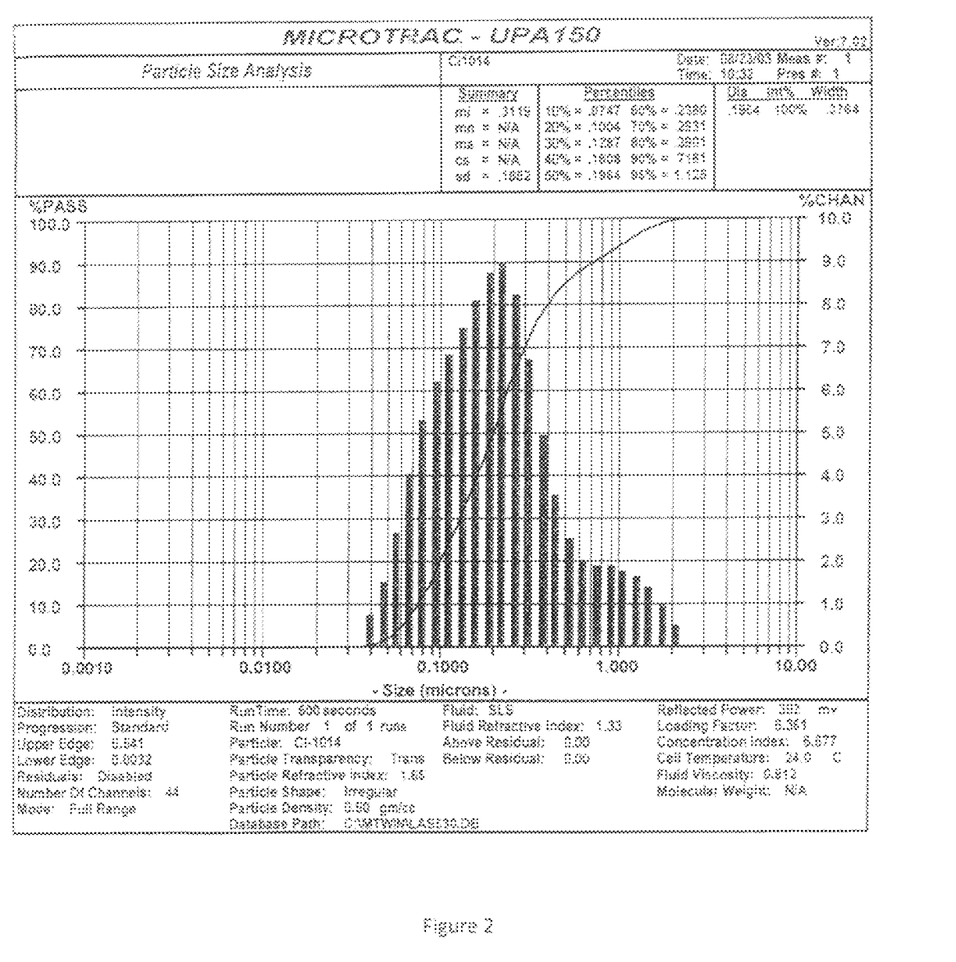
FIG. 2 of the drawings is a two-dimensional GPC chromatogram.

Previously nitrogen saturated 1-dodecene (82.58 g, 0.491 mol), silanic hydrogen intermediate Example 1 (200.0 g, 0.0981 mol), and allyl/OMe-PEO-12 (94.31 g, 0.157 mol) were combined in a Parr Model 4511 reactor and the head space was purged with nitrogen. The mixture was then stirred and heated to 85° C., whereupon the reactor was opened to allow for the injection of Pt catalyst (186.1 µL of a freshly prepared 0.050 M solution of $H_2PtCl_6.6H_2O$ in isopropyl alcohol). The reactor was sealed and the head space again purged with nitrogen while stirring was initiated, resulting in an exotherm leading to a rapid approximate 42° C. increase in temperature. After 30 minutes, the reactor was opened and nitrogen saturated allyl/OMe-PEO-12 (141.50 g, 0.235 mol) and additional Pt catalyst (79.7 µL) were added. The reactor was resealed and the stirred reaction allowed continued for an additional 60 minutes. By this time the reaction temperature was at 115° C. Next, the reactor was pressurized with 40 psi of ethylene and allowed to stir for an additional 60 minutes, during which time residual unreacted Si—H was consumed (monitored via IR spectroscopy). The maximum temperature reached during this interval was 119° C. The product, a clear, pale amber, not particularly viscous liquid, was removed from the reactor and degassed of saturated ethylene in vacuo. Proton NMR spectra of the product were consistent with the expected structure. GPC (8 mg/ml THF), shown below for this example, revealed an expected and acceptable molecular weight distribution and a low level of low molecular weight fraction. Particle size determination via dynamic laser light scattering for a 1% dispersion, shown below for this example, revealed a particle size distribution that was predominantly sub-micron. The GPC and light scattering result shown below for this example are typical of the other examples.

EXAMPLE 7

Copolymer where R=dodecyl, R'=Me, x=27, y=5, z+q=4, q≤0.8, p=12

Previously nitrogen saturated 1-dodecene (62.44 g, 0.371 mol), silanic hydrogen intermediate Example 3 (200.1 g, 0.0739 mol), and allyl/OMe-PEO-12 (71.23 g, 0.118 mol) were combined in a Parr Model 4511 reactor and the head space was purged with nitrogen. The mixture was then stirred and heated to 85° C., whereupon the reactor was opened to allow for the injection of Pt catalyst (225.7 µL of a freshly prepared 0.050 M solution of $H_2PtCl_6.6H_2O$ in isopropyl alcohol). The reactor was sealed and the head space again purged with nitrogen while stirring was initiated, resulting in an exotherm leading to a rapid approximate 31° C. increase in temperature. After 30 minutes, the reactor was opened and nitrogen saturated allyl/OMe-PEO-12 (144.15 g, 0.240 mol) were added. The reactor was resealed and the stirred reaction allowed continued for an additional 2 hours. By this time the reaction temperature was at 125° C. Next, the reactor was pressurized with 40 psi of ethylene and allowed to stir for an additional 1.5 hours, during which time residual unreacted Si—H was consumed (monitored via IR spectroscopy). The maximum temperature reached during this interval was 124° C. The product, a clear, pale amber, not particularly viscous liquid, was removed from the reactor and degassed of saturated ethylene in vacuo. Proton NMR spectra of the product were consistent with the expected structure.

EXAMPLE 8

Copolymer where R=dodecyl, R'=Me, x=18, y=4.25, z+q=4.75, q≤0.8, p=10

Previously nitrogen saturated 1-dodecene (103.40 g), silanic hydrogen intermediate Example 1 (294.62 g), and allyl/OMe-PEO-10 (140.79) were combined in a Parr Model 4511 reactor and the head space was purged with nitrogen. The mixture was then stirred and heated to 85° C., whereupon the reactor was opened to allow for the injection of Pt catalyst (384.4 µL of a freshly prepared 0.050 M solution of $H_2PtCl_6.6H_2O$ in isopropyl alcohol). A strong exotherm was noted. After 30 minutes, the reactor was opened and nitrogen saturated allyl/OMe-PEO-10 (211.18) were added. The reactor was resealed and the stirred reaction allowed continued for an additional 2 hours. By this time the reaction temperature was at 125° C. Next, the reactor was pressurized with 40 psi of ethylene and allowed to stir for an additional 1.5 hours, during which time residual unreacted Si—H was consumed (monitored via IR spectroscopy). The maximum temperature reached during this interval was 125° C. The product, a clear, pale amber, not particularly viscous liquid, was removed from the reactor and degassed of saturated ethylene in vacuo. Proton NMR spectra of the product were consistent with the expected structure.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the Doctrine of Equivalents.

What is claimed is:

1. A method for using an O/W formulation, comprising the steps of:
providing a compound represented by the following chemical structure in an O/W formulation:

wherein x=10-30,
wherein y=2-6,
wherein z+q=4-5(q≤0.8),
wherein p=12,
wherein R=dodecyl, and
wherein R'=H, Me
and applying the O/W formulation to the skin of a human.

* * * * *